(12) United States Patent
O'Leary

(10) Patent No.: US 8,453,649 B2
(45) Date of Patent: Jun. 4, 2013

(54) APPARATUS FOR POSITIONING A NASAL CANNULA

(75) Inventor: John P. O'Leary, Fort Collins, CO (US)

(73) Assignee: 0200L, LLC, Fort Collins, CO (US)

( * ) Notice: Subject to any disclaimer, the term of this patent is extended or adjusted under 35 U.S.C. 154(b) by 425 days.

(21) Appl. No.: 12/705,404

(22) Filed: Feb. 12, 2010

(65) Prior Publication Data
US 2010/0206312 A1   Aug. 19, 2010

Related U.S. Application Data

(60) Provisional application No. 61/207,842, filed on Feb. 18, 2009.

(51) Int. Cl.
*A61M 15/08* (2006.01)
(52) U.S. Cl.
USPC .................................. 128/207.18
(58) Field of Classification Search
USPC ........... 604/174; 128/207.11, 207.14, 207.17, 128/207.18
See application file for complete search history.

(56) References Cited

U.S. PATENT DOCUMENTS

| 4,367,735 | A | | 1/1983 | Dali |
|---|---|---|---|---|
| 5,117,818 | A | * | 6/1992 | Palfy .................. 128/204.11 |
| 5,513,635 | A | | 5/1996 | Bedi |
| 6,279,577 | B1 | | 8/2001 | Savaiano |
| 6,763,832 | B1 | | 7/2004 | Kirsch et al. |
| 6,986,353 | B2 | | 1/2006 | Wright |
| 7,007,694 | B2 | | 3/2006 | Aylsworth et al. |
| 2003/0056785 | A1 | | 3/2003 | Narihiko et al. |
| 2004/0187873 | A1 | | 9/2004 | Brown |
| 2005/0066976 | A1 | * | 3/2005 | Wondka .................. 128/207.18 |
| 2007/0095347 | A1 | | 5/2007 | Lampotang et al. |
| 2008/0078414 | A1 | * | 4/2008 | Demas .......................... 128/857 |
| 2008/0190436 | A1 | | 8/2008 | Jaffe et al. |
| 2010/0000534 | A1 | | 1/2010 | Kooij et al. |
| 2011/0197689 | A1 | | 8/2011 | Haveri et al. |

OTHER PUBLICATIONS

International Search Report for PCT/US10/24152, International Searching Authority, Apr. 26, 2010, pp. 1-9.
International Search Report, International Searching Authority, Apr. 3, 2012, pp. 1-15.

* cited by examiner

*Primary Examiner* — Theodore Stigell
(74) *Attorney, Agent, or Firm* — Samuel M. Freund; Cochran Freund & Young LLC

(57) ABSTRACT

A harness for securely positioning a nasal cannula on the face of a person for orally administering oxygen and other gases is described. A flexible chin strap adapted for placement around the chin of the person may be attached to adjustable, flexible straps effective for draping around the ears of the person, which are in turn attached to a central, cannula attachment portion disposed between the cannula and the face of the person. The gas delivery tubes of the cannula are also disposed behind the ears, essentially following the path of the flexible straps of the harness. Once placed on a person, the harness holds the nasal cannula such that the nasal prongs may disposed facing toward the mouth opening in the vicinity of the lower lip thereof, and may deliver gases to a mouth-breathing individual. Another embodiment of the harness may be utilized to position a nasal cannula for nasal administration of gas.

12 Claims, 5 Drawing Sheets

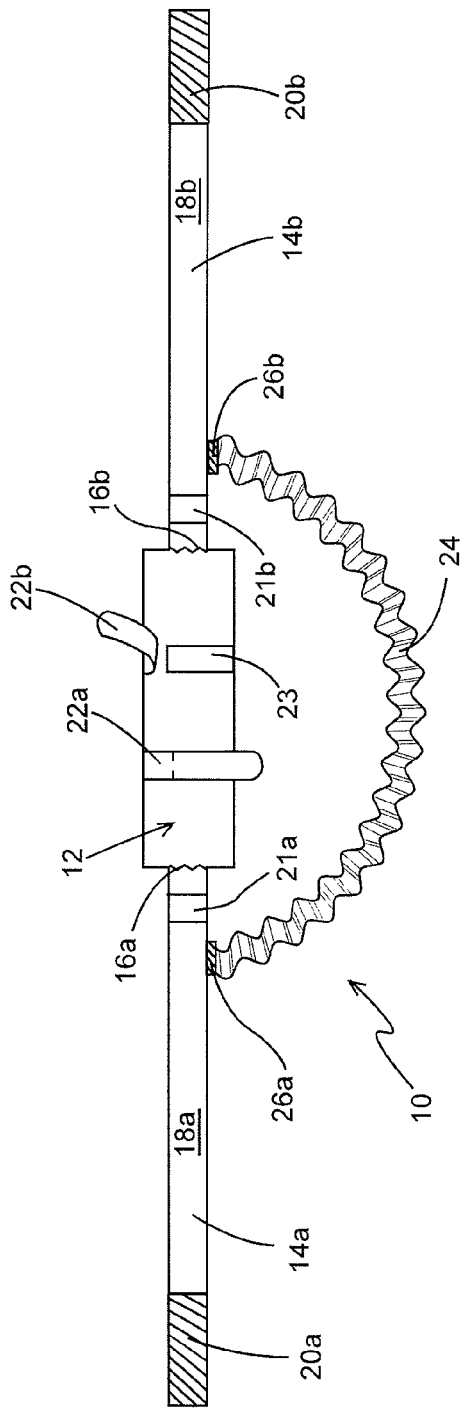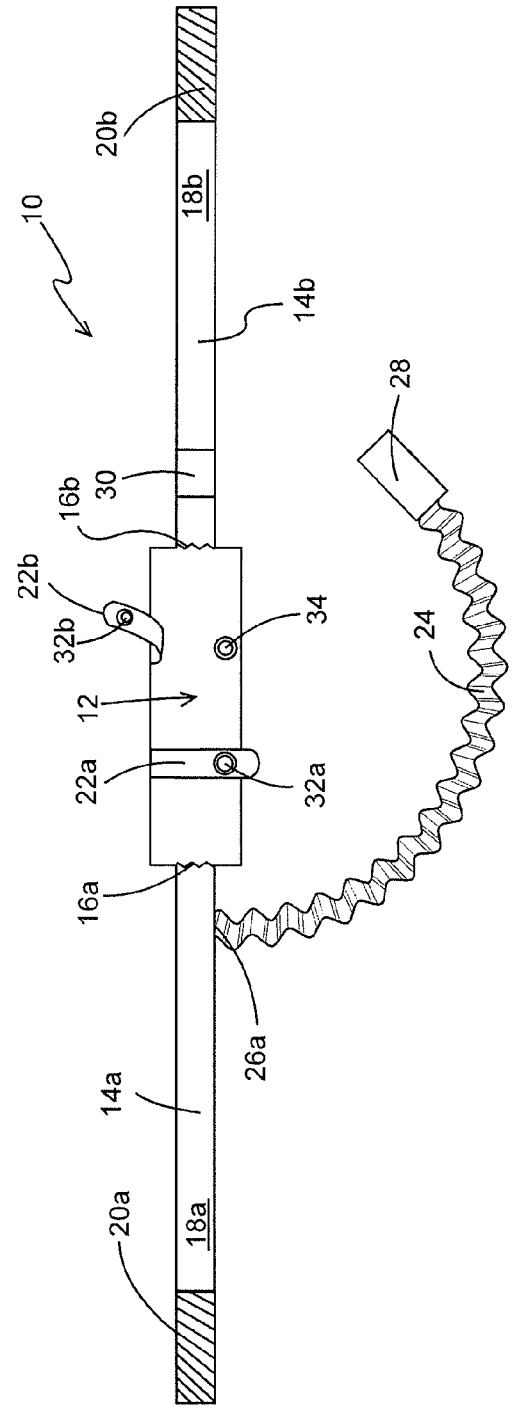

APPARATUS FOR POSITIONING A NASAL CANNULA

RELATED CASES

The present application claims the benefit of provisional patent application Ser. No. 61/207,842 for "Adjustable Chin Strap With Mounting Harness" by John P. O'Leary, filed on 18 Feb. 2009, which provisional application is hereby incorporated by reference herein for all that it discloses and teaches.

FIELD OF THE INVENTION

The present invention relates generally to nasal cannulas and, more particularly, to an apparatus for positioning a nasal cannula such that oxygen may be orally or nasally supplied to a person.

BACKGROUND OF THE INVENTION

Nasal cannulas are well-known devices for delivering low flows (1-6 l/min.) of supplemental or therapeutic oxygen to persons needing additional oxygen, where detailed control of respiration rate is not required. Such devices find significant use in elderly patients who need oxygen therapy. Typically, nasal cannulas include a hollow body portion having a pair of spaced-apart, curved elongated tubular portions (nasal interface or nasal prongs) extending through a surface of the body and in fluid communication with the hollow volume thereof. The tubular portions through which oxygen is caused to flow are adapted to fit into the nares of a person. Two plastic tubes in fluid contact with a source of oxygen are attached to the body, one at each end thereof, are disposed behind the ears of a person and brought into mechanical contact under the chin of the person by means of a loop adjustment collar or slide, as an example. Cannulas may be single lumen in which situation a single flow path exists between the patient and a source of oxygen, that is, the plastic tubes may merge into a single tube by means of a tee under the chin, as an example, or dual lumen where the flow paths to each naris may be separated by a barrier or bifurcation, and the two plastic tubes are supplied using different oxygen sources or gas regulators, as examples.

Oro-nasal cannulas are also known, although uncommon, wherein a third plastic tube is run parallel to one of the nasal supply tubes and mechanically coupled thereto. The third tube may be connected to a second or third oxygen source or gas regulator, depending upon the design of the nasal portion of the cannula. Through insertion of the tubular extensions into the flares, looping the oxygen supply tubes over the ears and combining the tubes under the chin, as an example, a nasal or oral-nasal cannula may be firmly affixed to a person, wherein it remains in place during periods of sleep or walking, as examples.

Patients undergoing continuous oximetry monitoring (measurement of oxygen saturation of the blood by means of an oximeter) often display desaturation while sleeping. Plethysmographic assessment of the individual generally uncovers no change in the air volume flowing, and the patient must be awakened and encouraged to breathe through the nose, wherein oxygen saturation improves. As the patient returns to sleep, the cannula remains in the nose, and desaturation returns. Thus, nasal cannulas positioned in the nares are ineffective for delivery of oxygen to mouth breathers. Further, breathing impairment conditions such as nasal/sinus congestion, nose bleeds, deviated septum, and nose injury, all prevent proper oxygen saturation using a nasal cannula positioned in the nares. An Oximizer® oxygen-conserving nasal cannula may be useful for better oxygen delivery at higher oxygen flow levels, but the difficulty remains for mouth breathing individuals and those with breathing impairments.

Oral oxygen delivery using masks (simple masks, face tents, and non-rebreather, venturi and BiPAP (Bi-level Positive Airway Pressure) masks, as examples) are an option. However, $CO_2$ retention, claustrophobia, drying of mucus membranes, communication difficulties, expense and considerable oxygen use make such options less attractive. High oxygen use is generally a problem with oro-nasal cannulas since the oxygen flow may ineffectively continue through the nasal portion of the cannula.

SUMMARY OF THE INVENTION

Accordingly, it is an object of embodiments of the present invention to provide a harness for positioning a nasal cannula for orally administering oxygen.

Another object of the invention is to provide a harness for positioning a nasal cannula for administering oxygen through the nose while reducing adverse effects to the surrounding skin.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects, and in accordance with the purposes of the present invention, as embodied and broadly described herein, the apparatus for positioning a nasal cannula on the face of a person for oral administration of gas, hereof, includes: a cannula support member having a first end and an opposing second end, and disposed between the nasal cannula and the face of the person; at least one flexible closure for securing the nasal cannula to the support member; a first strap attached at one end to the first end of the support member, and having a free distal end; a second strap attached at one end to the second end of the support member, and having a free distal end; and a chin strap attached to the first strap and the second strap and adapted for fitting around the chin of the person, whereby the first strap, the second strap and the chin strap are effective for securing the support member at a chosen location on the face of the person.

In another aspect of the present invention and in accordance with its objects and purposes, the apparatus for positioning a nasal cannula on the face of a person for oral administration of gas, hereof, includes: a cannula support member disposed between the nasal cannula and the face of the person, and having a first end and an opposing second end; a spring clip attached to the support member for securing the nasal cannula to the support member; a first strap attached at one end to the first end of the support member, and having a free distal end; a second strap attached at one end to the second end of the support member, and having a free distal end; and a chin strap attached to the first strap and the second strap, and adapted for fitting around the chin of the person, whereby the first strap, the second strap and the chin strap are effective for securing the support member at a chosen location on the face of the person In yet another aspect of the present invention and in accordance with its objects and purposes, the apparatus for positioning a nasal cannula on the face of a person for nasal administration of gas, hereof, includes: a cannula support member disposed between the nasal cannula and the face of the person, and having a first end and an opposing second end; at least one flexible closure for securing the nasal cannula to the support member; a first strap attached at one end to the first end of the support member, and having a free distal end; and a second strap attached at one end to the second end of the support member, and having a free distal end, whereby the first strap and the second strap are effective for securing the support member at a chosen location on the face of the person.

In still another aspect of the present invention and in accordance with its objects and purposes, the apparatus for positioning a nasal cannula on the face of a person for nasal administration of gas, hereof, includes: a cannula support member disposed between the nasal cannula and the face of the person, and having a first end and an opposing second end; a spring clip attached to the support member for securing the nasal cannula to the support member; a first strap attached at one end to the first end of the support member, and having a free distal end; and a second strap attached at one end to the second end of the support member, and having a free distal end, whereby the first strap and the second strap effective for securing the support member at a chosen location on the face of the person.

In another aspect of the invention and in accordance with its objects and purposes, the apparatus for positioning a nasal cannula on the face of a person for oral administration of gas, hereof, includes: a cannula support member disposed between the nasal cannula and the face of the person, the support member having a first end and an opposing second end; at least one flexible closure for securing the nasal cannula to the support member; a first strap having a closed loop portion adapted to fit over an ear of the person, and attached to the first end of the support member; a second strap having a closed loop portion adapted to fit over the other ear of the person, and attached to the second end of the support member; and a chin strap attached to the first strap and to the second strap adapted for fitting around the chin of the person, whereby the first strap, the second strap and the chin strap are effective for securing the support member at a chosen location on the face of the person.

In yet another aspect of the invention and in accordance with its objects and purposes, the apparatus for positioning a nasal cannula on the face of a person for oral administration of gas, hereof, includes: a cannula support member disposed between the nasal cannula and the face of the person, the support member having a first end and an opposing second end; a spring clip attached to the support member for securing the nasal cannula to the support member; a first strap having a closed loop portion adapted for fitting over an ear of the person, and attached one end of the support member; a second strap having a closed loop portion adapted for fitting over a second ear of the person, and attached to the second end of the support member; and a chin strap attached to the first strap and to the second strap adapted for fitting around the chin of the person, whereby the first strap, the second strap and the chin strap are effective for securing the support member at a chosen location on the face of the person.

Benefits and advantages of embodiments of the present invention include, but are not limited to, providing a harness for orally delivering gas to a person while overcoming the difficulty of maintaining a cannula in contact with bare skin, without the use of tape, and avoiding the adverse effects of plastic cannulae in long-term contact with bare skin, wherein the harness may also be used for positioning a nasal cannula for administering oxygen through the nose.

BRIEF DESCRIPTION OF THE DRAWINGS

The accompanying drawings, which are incorporated in and form a part of the specification, illustrate the embodiments of the present invention and, together with the description, serve to explain the principles of the invention. In the drawings:

FIG. 1A is a schematic representation of a front view of an embodiment of the present apparatus effective for positioning a nasal cannula for orally delivering oxygen to an individual illustrating the use of hook and loop closures for holding the nasal cannula on the cannula support member and for adjustably forming ear loops from straps attached to a cannula support member; FIG. 1B is a schematic representation of a front view of another embodiment of the present apparatus, illustrating snap closures for holding the nasal cannula on the cannula support member, and a detachable chin strap attached to the straps.

DETAILED DESCRIPTION OF THE INVENTION

Figure 1C:
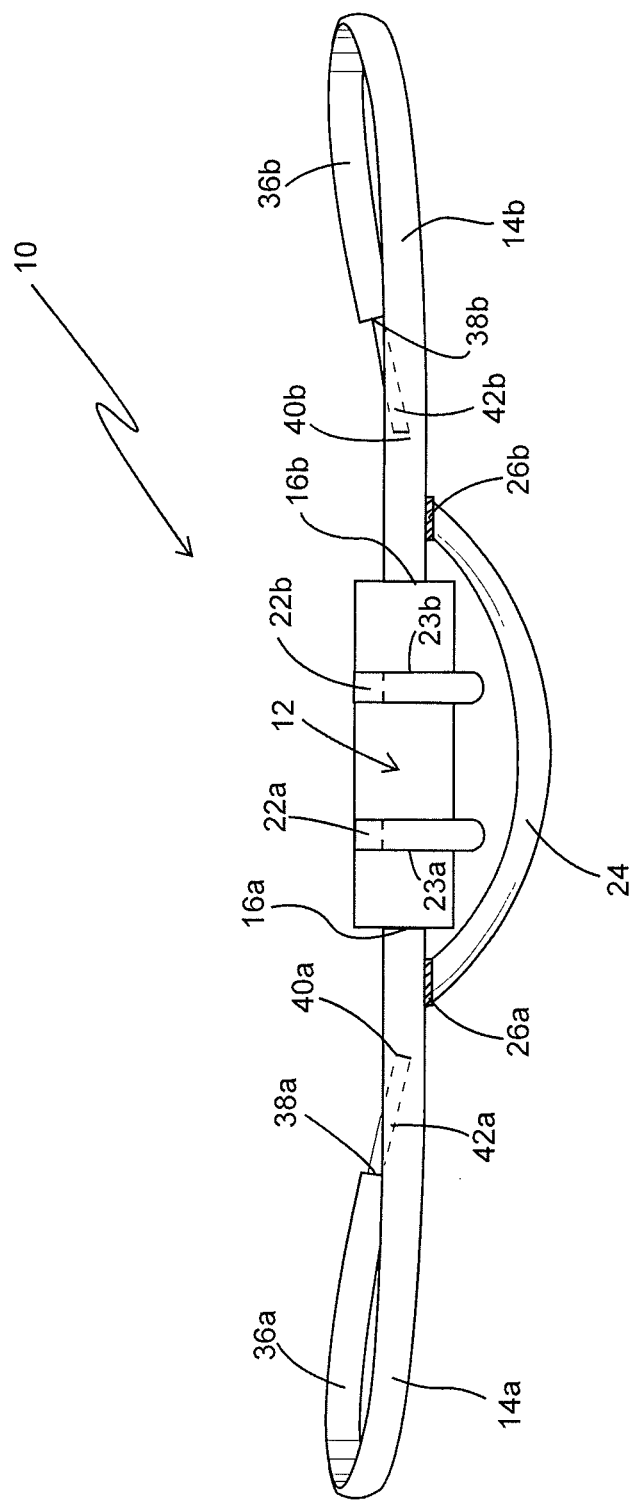
FIG. 1C is a schematic representation of still another embodiment of the present apparatus, illustrating flexible, loop-shaped straps elastically attached near the cannula support member for looping over the ears of a wearer.

Briefly, embodiments of the present invention include an apparatus for positioning a nasal cannula effective for oral delivery of oxygen to an individual. Mixtures of gases may also be administered using embodiments of the present invention. In an embodiment of the invention, a flexible chin strap is attached to adjustable, flexible straps effective for draping or looping around and behind the ears of a person, which are in turn attached to a central, cannula attachment/support member. The oxygen delivery tubes of the cannula may also be disposed behind the ears, essentially following the path of the flexible straps of the apparatus. Once placed on a person, the apparatus holds the nasal cannula such that the nasal prongs are disposed facing toward the mouth opening in the vicinity of the lower lip thereof, and may deliver oxygen to a mouth-breathing individual, while overcoming the difficulty of maintaining a cannula on a bare chin without the use of tape and the fact that the contour of the lower lip to the chin is oppositely shaped from the curvature of the cannula. Clearly, many means may be used to removably secure the straps at their loose, distal ends, for example, by tying or by using detachable clips, hooks, VELCRO® hook and loop fasteners, or similar connectors, such as screw connectors, as an example. Straps having preformed ear loops, elastically attached near the cannula support member are described below.

Reference will now be made in detail to the present embodiments of the invention, examples of which are illustrated in the accompanying drawings. In the FIGURES, similar structure will be identified using identical reference characters. Turning now to FIG. 1A, cannula positioning apparatus, 10, hereof, includes cannula support member, 12, to which flexible straps, 14a, and, 14b, are either attached at locations, 16a, and 16b, respectively, or integrally formed therewith. Body portions, 18a, and, 18b, respectively, of straps 14a and 14b may be made of material effective for attachment by hook portions, 20a, and, 20b, respectively, of VELCRO® hook and loop closures, disposed near the free, distal ends thereof, for adjusting the dimensions of loops formed by straps 14a and 14b to comfortably and securely fit over and behind a person's ears. Other materials may be used when loop materials, 21a, and, 21b, of VELCRO® hook and loop closures are attached to straps 14a and 14b, respectively. Fastening tabs, 22a, and, 22b, for holding a nasal cannula are attached to cannula support member 12, and are fastened to support 12 by hook and loop closures, as an example. Tab 22b is shown in an open configuration with matching patch, 23b, affixed to member 12 such that a hook and loop closure may be formed. After placement of a cannula under the tab, the tab may be closed. Corresponding patch 23a is affixed to member 12 for cooperation with tab 22a. A single tab closure embodiment (not shown in FIG. 1A) may effectively be used for holding a nasal cannula by placing the cannula such that the tab is disposed between the tubular portions of the cannula extending from the base thereof, as an example.

Chin strap, 24, attached at locations, 26a and 26b of support member 12, may be formed from elastic material, or may be otherwise adjustable such that a comfortable and secure fit around a wearer's chin may be achieved. As shown in FIG. 1B, chin strap 24 may be detachable at location 26b, using hook portion, 28, from hook and loop closure material, as an example, if straps 14a and 14b are made of material effective for attachment by hook portions. Loop portion, 30, from hook and loop closure material may be attached to strap 14b if other materials are used such that cooperation with hook portion 28 may be achieved. Clearly other fastening means may be used to achieve this removable attachment. Snap closures, not shown in FIG. 1B, are also anticipated. Snaps, 32a, and, 32b, are illustrated in FIG. 1B for closing nasal cannula holding tabs 22a and 22b, respectively, as another example of means for securely holding a nasal cannula. Tab 22b is shown in an open configuration with matching snap, 34, attached to member 12.

FIG. 1C is a schematic representation of another embodiment of the apparatus hereof showing straps 14a and 14b formed into loops, 36a, and, 36b, by attaching ends, 38a, and, 38b, at locations, 40a, and 40b, respectively. Shown in FIG. 1C are elastic portions, 42a, and 42b, for permitting the apparatus to be used for various head sizes.

Support member 12, straps 14a and 14b, and chin strap 24 may be fabricated from various materials including, but not limited to, doe-suede, cotton, neoprene, foam, fleece, felt, Teri-cloth, and polyester, as examples. Spandex and panty hose materials may be used for elastic embodiments of straps 14a and 14b and chin strap 24. It is desirable, however, to avoid the use of plastic next to a person's skin in the vicinity of the nose and mouth.

Figure 2:
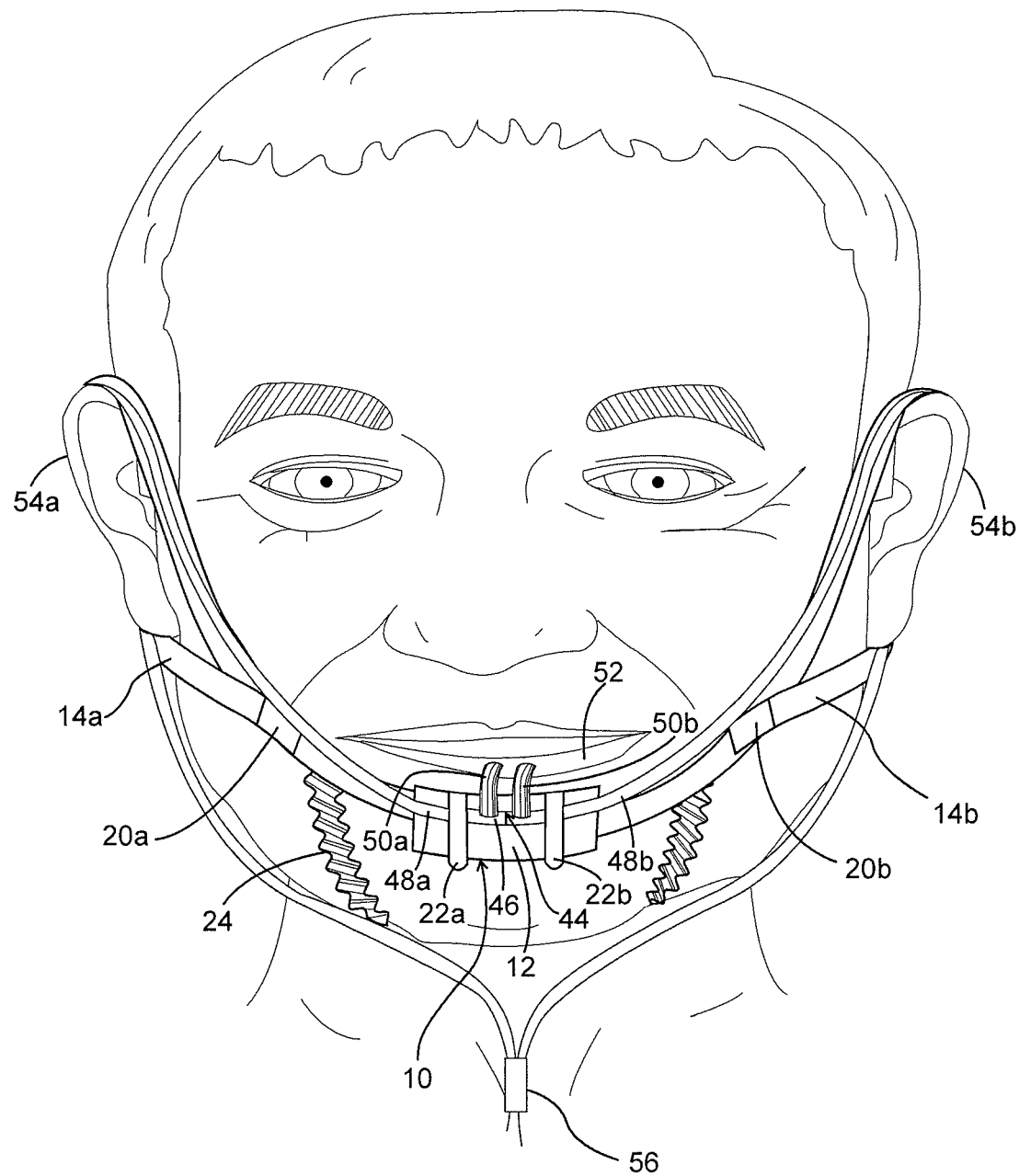
FIG. 2 is a schematic representation of a front view of the harness illustrated in FIG. 1 hereof in use for positioning a nasal cannula in the vicinity of the lower lip of an individual.

FIG. 2 is a schematic representation of a front view of the embodiment of apparatus 10 shown in FIG. 1A hereof, illustrating the use thereof by an individual. Commercially available nasal cannula, 44, having base, 46, and oxygen delivery tubes, 48a, and, 48b, is shown as held in place on cannula support member 12 using tabs 22a and 22b, respectively, such that nasal interface or nasal prongs, 50a, and, 50b, are firmly located in the region of lower lip, 52, of the patient such that oxygen may be orally delivered to the patient, support member 12 being disposed between the cannula and the face of the person. Oxygen delivery tubes 48a and 48b are shown as looped over and behind the patient's ears, 54a, and, 54b, respectively, and secured using slide, 56. Straps 14a and 14b are also shown as looped over and behind ears 54a and 54b and fastened using VELCRO® hook and loop closures 20a and 20b, respectively.

Figure 3:
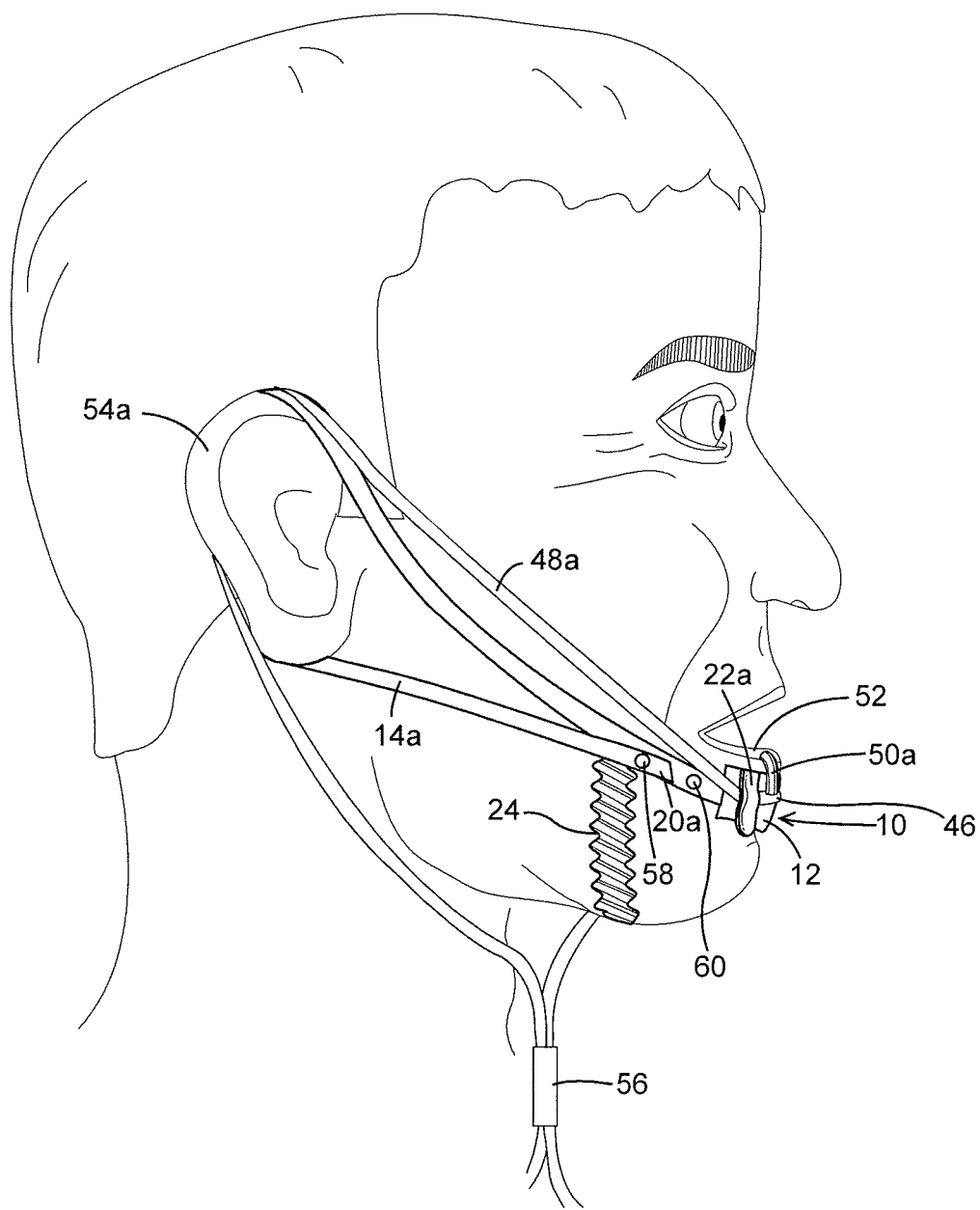
FIG. 3 is a schematic representation of a side view of the harness illustrated in FIG. 1 hereof in use for positioning a nasal cannula in the vicinity of the lower lip of an individual.

FIG. 3 is a schematic representation of a side view of apparatus 10 shown in FIG. 2 hereof, showing strap 14a being attached to itself using snap, 58. Additional, corresponding snap portions, 60, as an example, may be placed along strap 14a (and 14b, not shown in FIG. 3) for adjusting the length of the straps to fit various head sizes. Straps 14a and 14b may also be wrapped around the head of the patient, if the patient finds this to be more comfortable either using snap closures (58, 60), or the hook portion of hook and loop closures, or VELCRO® hook and loop closures, depending on the material used, as examples.

Figure 4:
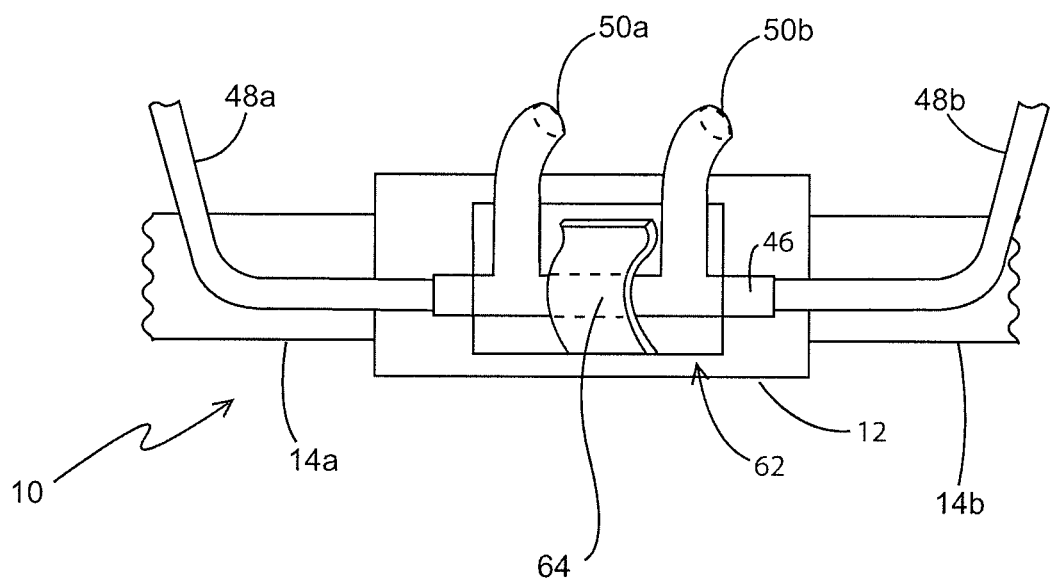
FIG. 4 is a schematic representation of a perspective view of a clip embodiment of the positioning apparatus hereof illustrating a standard nasal cannula held in place by a clip affixed to the cannula support member.

FIG. 4 is a schematic representation of a perspective view of a clip embodiment of the positioning apparatus hereof illustrating standard nasal cannula 44 having base 46 held in place by spring clip assembly, 62, wherein clip, 64, is attached to base, 66, affixed to cannula support member 12. Cannula 44 may be oriented either as shown in FIG. 4 or rotated by 180° relative to spring clip 64. Spring clip assembly 62 may be made from plastic or metal, as examples.

Returning to the FIGURES, chin strap 24 may be removed from support member 12, and member 12 may be deployed with commercially available nasal cannula 44 against the upper lip of a patient for providing secure orientation of the nasal cannula in the nose of a patient and protection from skin irritation with prolonged use of the nasal cannula.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. Apparatus for positioning a nasal cannula on the face of a person for oral administration of gas, comprising:
    a cannula support member disposed between said nasal cannula and the face of said person, and having a first end and an opposing second end;
    at least one flexible closure for securing said nasal cannula to said support member;
    a first strap attached at one end to the first end of said support, and having a free distal end;
    a second strap attached at one end to the second end of said support member, and having a free distal end; and
    a chin strap attached to said first strap and to said second strap adapted for fitting around the chin of said person, whereby said first strap, said second strap and said chin strap are effective for securing said support member at a chosen location on the face of said person.

2. The apparatus of claim 1, further comprising means for forming a loop in each of said first strap and said second strap effective for fitting around an ear of said person.

3. The apparatus of claim 1, further comprising means for fastening said first strap and said second strap together in the vicinity of the distal end thereof around the head of said person.

4. The apparatus of claim 1, wherein said chin strap is elastic.

5. Apparatus for positioning a nasal cannula on the face of a person for oral administration of gas, comprising:
    a cannula support member disposed between said nasal cannula and the face of said person, and having a first end and an opposing second end;

a spring clip attached to said support member for securing said nasal cannula to said support member;

a first strap attached at one end to the first end of said support member, and having a free distal end;

a second strap attached at one end to the second end of said support member, and having a free distal end; and a chin strap attached to said first strap and to said second strap adapted for fitting around the chin of said person, whereby said first strap, said second strap and said chin strap are effective for securing said support member at a chosen location on the face of said person.

6. The apparatus of claim 5, further comprising means for forming a loop in each of said first strap and said second strap effective for fitting around an ear of said person.

7. The apparatus of claim 5, further comprising means for fastening said first strap and said second strap together in the vicinity of the distal end thereof around the head of said person.

8. The apparatus of claim 5, wherein said chin strap is elastic.

9. Apparatus for positioning a nasal cannula on the face of a person for oral administration of gas, comprising:

a cannula support member disposed between said nasal cannula and the face of said person, said support member having a first end and an opposing second end;

at least one flexible closure for securing said nasal cannula to said support member;

a first strap having a closed loop portion adapted to fit over an ear of said person, and attached to the first end of said support member;

a second strap having a closed loop portion adapted to fit over a second ear of said person, and attached to the second end of said support member; and a chin strap attached to said first strap and to said second strap adapted for fitting around the chin of said person, whereby said first strap, said second strap and said chin strap are effective for securing said support member at a chosen location on the face of said person.

10. The apparatus of claim 9, wherein said chin strap is elastic.

11. Apparatus for positioning a nasal cannula on the face of a person for oral administration of gas, comprising:

a cannula support member disposed between said nasal cannula and the face of said person, said support member having a first end and an opposing second end;

a spring clip attached to said support member for securing said nasal cannula to said support member;

a first strap having a closed loop portion adapted for fitting over an ear of said person, and attached one end of said support member;

a second strap having a closed loop portion adapted for fitting over a second ear of said person, and attached to the second end of said support member; and a chin strap attached to said first strap and to said second strap adapted for fitting around the chin of said person, whereby said first strap, said second strap and said chin strap are effective for securing said support member at a chosen location on the face of said person.

12. The apparatus of claim 11, wherein said chin strap is elastic.

* * * * *